United States Patent [19]

Rosen

[11] Patent Number: 5,256,397
[45] Date of Patent: Oct. 26, 1993

[54] 2,2,5,5-TETRASUBSTITUTED-PYRROLIDINE-1-OXYL COMPOUNDS USEFUL AS MRI AGENTS

[75] Inventor: Gerald M. Rosen, Lutherville, Md.

[73] Assignee: M.R.I., Inc., Lutherville, Md.

[21] Appl. No.: 862,031

[22] Filed: Apr. 2, 1992

Related U.S. Application Data

[63] Continuation-in-part of Ser. No. 485,068, Feb. 26, 1990, Pat. No. 5,104,641, which is a continuation-in-part of Ser. No. 121,823, Nov. 6, 1987, abandoned, and a continuation-in-part of Ser. No. 836,867, Mar. 7, 1986, Pat. No. 4,834,964.

[51] Int. Cl.$^5$ .................. G01N 24/08; A61K 31/40; C07D 207/46
[52] U.S. Cl. ..................... 424/9; 128/653.4; 436/173; 514/424; 548/542
[58] Field of Search .............. 424/9; 128/653.4, 653.3, 128/654; 436/173; 514/424; 548/542

[56] References Cited

U.S. PATENT DOCUMENTS

| | | | |
|---|---|---|---|
| 3,502,692 | 3/1970 | Feldman et al. | 548/531 |
| 4,656,026 | 4/1987 | Coffman et al. | 424/9 |
| 4,834,964 | 5/1989 | Rosen | 424/9 |
| 5,104,641 | 4/1992 | Rosen | 424/9 |

OTHER PUBLICATIONS

Stier et al. *Xenobiotica* 1(4/5): 499-500 (1971).
Rauckman et al. *Spin Labeling in Pharmacology* 175-190 (1984).
Rosen et al. *Biochim. Biophys. Acta.* 969:236-41 (1988).
Kruch, T. R. *Spin Labeling Theory & Applications* 339-372 (1976).
Griffeth et al. *Investigative Radiology* 19:1533 (1984).
Brasch, R. *Excerpta Medica* pp. 11-13 (1986).
Rosen et al. *Biochem. Pharmacol.* 26:675-8 (1977).
Rosen et al. *Radiology* 163:239-245 (1987).
Rauckman et al. *J. Med. Chem.* 19(10):1254-6 (1976).
Rosen, G. M. *J. Med. Chem* 17(3):358-60 (1974).
Keana et al. *Magn. Res. Med.* 5:525-36 (1987).
Keana, John F. 78(1):37-64 (1978).
Couet, W. R. et al. *Pharaceutical Research* pp. 203-209 (1984).
Shapiro, A. B. *Chem. Abs.* CA87(5):346765q (1977).
Brasch, R. C. *Radiology* 147:773-779 (1983).

*Primary Examiner*—Richard L. Raymond
*Assistant Examiner*—Gary E. Hollinden
*Attorney, Agent, or Firm*—Millen, White, Zelano, & Branigan

[57] ABSTRACT

Nitroxides useful as MRI enhancing agents are of the formula

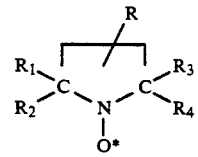

wherein $R_1$, $R_2$, $R_3$ and $R_4$ each are alkyl of 1-4 carbon atoms; and R is —alk—COO$^-$M$^+$ or —B—N$^+$(Alk)$_3$Hal$^-$ in which alk is alkylene of 1-8 carbon atoms, B is a divalent bond or alkylene of 1-8 carbon atoms, M$^+$ is an ammonium or metal ion, Alk is alkyl of 1-8 carbon atoms or a corresponding alkyl group substituted by a free or esterified hydroxy group, and Hal$^-$ is Cl$^-$, Br$^-$ or I$^-$.

12 Claims, No Drawings

2,2,5,5-TETRASUBSTITUTED-PYRROLIDINE-1-OXYL COMPOUNDS USEFUL AS MRI AGENTS

BACKGROUND OF THE INVENTION

This invention relates to novel 2,2,5,5-tetrasubstituted-pyrrolidine-1-oxyl compounds which are useful as magnetic resonance imaging (MRI) (NMR contrast enhancing) agents, especially for blood containing portions of the body and joints. This is a continuation-in-part of Ser. No. 07/485,068, filed Feb. 26, 1990 (now U.S. Pat. No. 5,104,641) which is a continuation-in-part of Ser. No. 07/121,823, filed Nov. 6, 1987 now abandoned, as a continuation-in-part of Ser. No. 07/836,867, filed Mar. 7, 1986, now U.S. Pat. No. 4,834,964.

NMR imaging agents are, by definition, paramagnetic, i.e., they have an unpaired electron. Nitroxides have the theoretical potential for use commercially as in vivo NMR contrast enhancing agents because they meet several of the criteria required for all such products, e.g., prolonged storage stability at varying pH and temperature, feasible methods of preparation, good shelf life, chemical flexibility which permits structural variation to adapt to specific end-use environments, and longer spin relaxation times compared to inorganic paramagnetic ions. However, nitroxides generally are not practical for such use because they are rapidly enzymatically reduced in tissues to products which do not enhance the NMR signal. See "Pharmacokinetics of Nitroxide NMR Contrast Agents," Griffeth et al., *Invest. Radiol.* 19:553–562 (1984), of which I am coauthor. Brasch, et al., in Radiology 147:773–779 (1983), report the successful enhancement of an NMR image with "TES", a piperidine mononitroxide stable free radical. Although that compound is stated by the authors to have an in vivo half life of 38 minutes, the dosage employed by them to achieve a substantial increase in intensity of signal from the renal parenchyma was huge, viz., 0.5 g/kg body weight by intravenous injection. Such a high dose suggests that the authors compensated for the rapid enzymatic reduction of the nitroxide by the use of such a massive dose of the nitroxide that it overwhelmed reductases in the tissue under study. I have found that unless the enzyme system is overwhelmed in this manner, the in vivo reduction of virtually all nitroxides is virtually instantaneous. Needless to say, such a procedure is contraindicated for human use. Because of the relatively low electrochemical potential, viz., about 300 mV, which is characteristic of all nitroxides having an isolated nitroxide group, the rapid enzymatic reduction and, accordingly, their limited half-life at acceptably low blood levels, have rendered nitroxides as a class poor candidates as commercially useful medical NMR image enhancing agents.

Brasch et al., "Brain Nuclear Magnetic Resonance Imaging Enhanced by a Paramagnetic Nitroxide Contrast Agent: Preliminary Report," AJR 141, Nov. 1983, pp. 1019–1023; ibid., Radiology, 147:773–779, June 1983, and Brasch, in an article entitled "An Overview of Contrast Agents for Magnetic Resonance Imaging," in the text "Contrast Agents in Magnetic Resonance Imaging" (Excerpt Medica Publisher, 1986) report MRI animal studies on PCA (2,2,5,5-tetramethylpyrrolidine-1-oxyl-3-carboxylic acid) and TES (N-succinyl-4-amino-2,2,6,6-tetramethylpiperidine-1-oxyl). The activities reported are exceptions to the general rule with respect to the in vivo stability of nitroxides as a class.

Feldman et al., U.S. Pat. No. 3,502,692, and Keana et al., "Magnetic Resonance in Medicine," 5, 525–536 (1987), disclose nitroxides employed in the MR imaging process of U.S. application Ser. No. 07/485,068.

U.S. Pat. No. 3,704,235 is concerned with the preparation of tropane nitroxides. These compounds are quite toxic because they are reduced by enzymes such as FAD-containing monooxygenase to give superoxide. They are also too unstable to have a useful half-life in vivo.

U.S. Pat. No. 3,716,335 relates to the use of nitroxides as sensors of certain electron transfer reactions and is not related to the use of nitroxides as NMR contrast enhancing agents.

U.S Pat. No. 3,702,831 relates to the use of nitroxides as magnetometer to monitor magnetic fields. This is only remotely related in that the magnetic field set-up by the free radical interacts with an applied field. Thus, the nitroxide becomes a marker, a probe. The compound used, viz., di-tert-butylnitroxide is rapidly eliminated in vivo.

U.S. Pat. No. 4,099,918 describes the synthesis of pyrrolidinoxyl as probes to study biological systems. There is no mention in this patent of NMR enhancing activity. Nitroxides have been used for years as probes of membrane structure.

Published European Patent Appln. 84 10 890.6 discloses as stable NMR image enhancing agents nitroxides of the formula

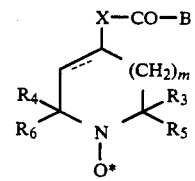

wherein B is a protein, sugar or lipid residue or —NR$_1$R$_2$.

Chem. Abstr. 88:134654s discloses 2,2,5,5-tetramethylpyrrolinyl-1-oxyl-saccharides.

Chem. Abstr. 90:137610b discloses a nitroxide of the formula

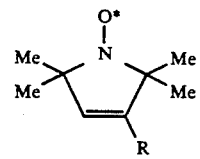

wherein R is —COOH or —CONH—C(CH$_3$)$_2$—OH.

French Application No. 73 23978 (Publication No. 2,235,103) discloses nitroxides of the formula

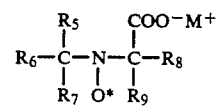

wherein R$_1$, R$_2$, R$_3$ and R$_4$ are alkyl.

Golding, B. T. et al, Synthesis, 1975, No. 7, 462–433, discloses various nitroxides, including 2,2,5,5-pyrrolinyl-oxyls of the formula

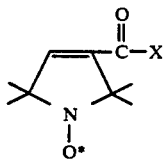

wherein X is OH, Cl, OC₂H₅, piperidino, anilino, benzylamino, hydroxyethylamino or carbethoxymethylamino.

I have found that although in general nitroxides have too short a half-life in blood to be useful as vascular NMR contrast enhancing agents, surprisingly within these classifiable are classes of nitroxides which are useful as vascular NMR contrast enhancing agents, as well as contrast enhancing agents for joints such as the knee.

OBJECTS OF THE INVENTION

It is an object of this invention to provide charged stable organic nitroxide NMR contrast enhancing agents, e.g., of a blood-containing portion of the body of a vertebrate, and especially for soft abdomen tissues (e.g., kidneys, spleen) and joints (e.g., knee). Other objects will be apparent to those skilled in the art to which this invention pertains.

SUMMARY OF THE INVENTION

In a composition aspect, this invention relates to novel NMR charged, stable organic nitroxides of the formula:

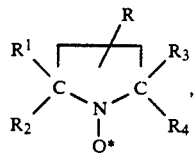

(I)

wherein $R_1$, $R_2$, $R_3$ and $R_4$ each are alkyl of 1–4 carbon atoms; and R is —alk—COO⁻M⁺ or —B—N⁺(Alk)₃Hal⁻ in which alk is alkylene of 1–8 carbon atoms, B is a divalent bond or alkylene of 1–8 carbon atoms, M+ is an ammonium or metal ion, Alk is alkyl of 1–8 carbon atoms or a corresponding alkyl group substituted by a free or esterified hydroxy group, and Hal⁻ is Cl⁻, Br⁻ or I⁻.

DETAILED DISCUSSION

The term "charged" nitroxide as used herein means the nitroxide compound possesses, in addition to the nitroxyl group, a functional group which at physiological pH possesses a charge, either positive or negative, e.g., a carboxylic acid group or a quaternary ammonium group. Preferably, the nitroxide is fully charged, i.e., it is not in equilibrium with a non-charged species. Thus, quaternary ammonium nitroxides are preferred over carboxylic acids which, in turn, are preferred over primary, secondary and tertiary amines. Of the acidic nitroxides in equilibrium with a non-changed species, preferred are those having a pKa of less than 7.4, more preferably less than 5. Of the basic nitroxides, those with pKa greater than 7.4 are preferred.

The term "stable" as used herein means the nitroxide molecule totally and the nitroxyl moiety especially has an acceptable half-life when stored under ambient conditions, e.g., greater than 2 years and preferably greater than 5 years and when in aqueous solution is stable at room temperature for at least 2 hours and preferably at least 8 hours.

The term "neurologically acceptable" means that the nitroxide produces no short or long term adverse neurological effects. The term "non-toxic" means that no local or systemic toxic effects are manifested in the host by the nitroxide at the dosages required to achieve MRI enhancement.

The charged nitroxides of this invention have certain structural features in common. As is well known, to be a stable free radical, both carbon atoms alpha to the nitroxyl group ordinarily must be fully substituted, i.e., they bear no hydrogen atoms, except a single hydrogen atom may be present if it is prevented from interacting with the nitroxyl group, e.g., by being acidic enough to be replaceable by a sodium ion. The simplest such substituents are alkyl, preferably of 1–8 carbon atoms, e.g., $CH_3$, $C_2H_5$, propyl, 2-propyl, butyl, 2-butyl, heptyl, octyl, etc., groups although other groups, such as alkyl groups substituted by one or more of hydroxy, halo, acyloxy, or a carbocyclic or heterocyclic aryl group, e.g., phenyl or pyridyl, may be present instead. Another requirement is that the nitroxide be water soluble. Ordinarily, the group imparting the requisite charge to the nitroxide compound, e.g., a carbocyclic, sulfonic or phosphonic acid or quaternary ammonium group will impart the requisite solubility thereto. However, other solubilizing groups may also be present in the molecule, if desired.

The preferred charged nitroxides of this invention are very water soluble, e.g., at least one μmole/ml., and preferably also have a low molecular weight, e.g., less than about 350, not including any associated metal or halogen ion, and are heterocyclic, preferably with only the nitroxide nitrogen atom as a hetero ring atom.

As stated above, physiologically the nitroxides of this invention are both neurologically and physiologically non-toxic and preferably are pharmacologically substantially inactive, at least at the minimum concentration required to achieve the desired image enhancement, and those of Formula I are resistant to rapid biodegradation by normal body mechanisms when injected into the blood stream. They are free of heavy metals, thereby avoiding the potential of residual mutagenic effects.

Examples of charged nitroxides of Formula I which meet the foregoing criteria are those wherein $R_1$, $R_2$, $R_3$ and $R_4$ each are $CH_3$ or $C_2H_5$; those wherein $R_1$, $R_2$, $R_3$ and $R_4$ each are $CH_3$ and R is —alk—COO⁻M⁺ in which alk is alkylene of 1–4, preferably 2–4, carbon atoms and M⁺ is Na⁺ or K⁺; and those wherein each of $R_1$, $R_2$, $R_3$ and $R_4$ is $CH_3$ and R is —B—N⁺(Alk)₃Hal⁻ in which B is a divalent bond or alkylene of 1–8, preferably 1–4, carbon atoms, and each Alk is alkyl of 1–8, preferably 1–4, carbon atoms, e.g., methyl or ethyl, and Hal⁻ is Cl⁻, Br⁻ or I⁻.

The nitroxides of this invention can be prepared in a variety of ways known in the prior art to be useful for the production of substituted nitroxides, e.g., as described in the publications cited hereinabove. An example of a synthetic route to the nitroxides of Formula I wherein $R_1$, $R_2$, $R_3$ and $R_4$ are alkyl can be shown schematically as follows:

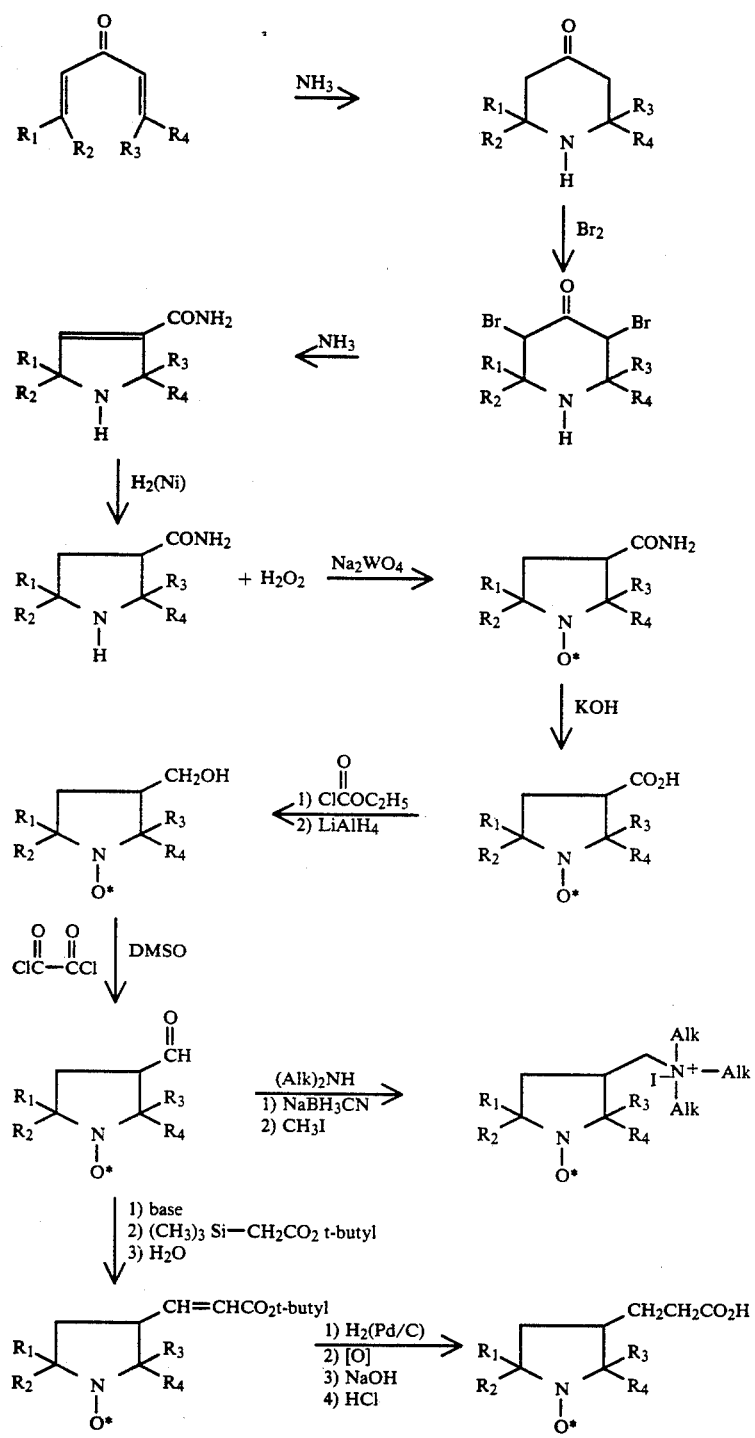

Contemplated equivalents of the compounds of the nitroxides employed in this invention are nitroxides bearing an additional substituent on a ring carbon atom thereof, e.g., alkyl, alkoxy, carboxy, carbalkoxy, halogen, nitro, etc., or instead of a group present thereon, a simple derivative thereof, e.g., an esterified hydroxy or carboxy group, an etherified hydroxy group, a halogenated or oxygenated alkyl group, provided water solubility and charge stability are not adversely affected.

The nitroxides of formula I of this invention are useful as an enhancing agent for MRI on joints. The most common use of this type of agent is assisting in the diagnosis of the extent of degeneration of or damage to a joint and/or the extent of recovery therefrom during chemo- or physiotherapy. Although MRI of a joint without the aid of an enhancing agent is possible, the use of an enhancing agent of this invention allows one to gain useful information while employing $T_1$-weighted imaging with its inherent high signal-to-noise ratio, thus making MRI a much more valuable diagnostic modality in the evaluation of this pathology.

The nitroxyl compounds of this invention are useful as enhancing agents for MRI of all vertebrates, i.e., in addition to human beings, other mammals and non-mammals.

The compounds of Formula (I) are "bioreductive resistant" and thus can be used to enhance MRI on joints and organs to which the nitroxide can be delivered by injection into the blood stream. For example, they can be used for the following purposes:

(a) Evaluating brain tumors and infarction, the latter being quite important because diffusion across the blood-brain barrier is dependent upon the structure of the nitroxide and the breakage of the barrier. For example, if there is a breakage due to an infarction, a charged, bioreductive-resistant nitroxide can enter the brain where otherwise the barrier prevents such diffusion.

(b) As contrast enhancement agents of body/abdominal MRI. For example, depending upon charge, a number of these agents are taken up by the kidney and excreted. The high concentration of the nitroxides (noted, below) in the urine attests to the rapid elimination by the kidney, and permits MRI of the bladder. These agents are useful for detection and differentiation of renal mass lesions, separation of adjacent structures, and assessment of the ureters and bladder, in a manner presently used for CAT scan and iodinated contrast agents. Similarly, such nitroxides are useful for contrast enhancement of other abdominal or retroperitoneal tissues.

(c) When bound to (or in) a colloidal or liposomal vehicle they are taken up by the reticuloendothelial system (RES) and thus are useful for detection of mass lesions or other pathological processes in the liver and spleen.

(d) Depending on structure they can be used to monitor pathologic states, e.g., hepatobiliary obstruction, renal ischemia/infarction, ureteral obstruction, as well as other tumors.

(e) As contrast enhancing agents on joints. For example, to determine the amount of inflammation in a knee.

The nitroxyl compound preferably is administered by injection as a single dose but can be administered in multiple doses or by continuous drip, e.g., in situations where MRI scans over several hours are contemplated. The amount administered is preferably that which achieves greater than 5%, preferably at least a 10% and more preferably at least 20% reduction in the T1 relaxation time of the fluid in the area being scanned. Desirably in humans an initial dose of at least about 0.04 mmole is employed, e.g., from about 0.05 to 2 mmoles. Generally, individual doses of about 2–100 mg, preferably about 5–50 mg, are employed, depending on whether a joint or an organ is to be imaged.

For a description of the use of a nitroxide as an MRI enhancing agent for renal structures, see Brasch, R. C. et al. Radiology 1983, 147:773–779. When the heart or a portion of the cardiovascular system of a human being is to be imaged, the intravenous dosage of the nitroxyl compound generally will be about 1 to 5 g., e.g., about 1 to 10 mmol/kg.

The nitroxyl compound is ordinarily injected as a solution in a non-toxic injectable pharmacologically acceptable sterile aqueous vehicle, e.g., distilled water, physiological saline solution, or fluid withdrawn from the joint to be MRI scanned, or a mixture of either of the latter two and either of the former two. The aqueous vehicle can also contain other ingredients conventionally present in diagnostic fluids injected into the spine or blood, e.g., NaCl, buffer, etc.

The nitroxides of Formula (I) of this invention can be employed as pharmaceutical compositions adapted for injection into the blood or joint, e.g., those comprising an amount of a sterile solution of a concentration of about 1 to 50 mM, preferably about 10 mM, in an aqueous vehicle, of a charged organic nitroxide of Formula (I) effective to reduce the relaxation time of the area under study during the scanning period sufficiently to enhance the image produced by the MRI scanning. For example, the nitroxide or a solution thereof can be contained in sterile form in a conventional sealed ampoule or vial, in single or multiple dosage form, and can be at the desired injection concentration or it can be in a more concentrated form so that it can be mixed with the aqueous vehicle prior to injection.

The nitroxides of this invention can be employed as pharmaceutical compositions adapted for intravenous injection comprising a sterile solution in an aqueous vehicle at a concentration effective to reduce the relaxation time of at least one of blood and urine during the MRI scanning period sufficiently to enhance the image produced by the MRI scanning of the blood or urine of a mammal intravenously injected with the composition, of a compound of Formula I.

The nitroxides of this invention can also be employed to enhance the image obtained by NMR scanning of the blood, urine or an organ associated with the cardiovascular system of an animal, which comprises injecting into the blood of the animal, prior to the MRI scan of the portion of the body to be imaged, in admixture with a nontoxic injectable pharmacologically acceptable aqueous vehicle, an amount effective during the scanning period to reduce the relaxation time of the fluid in the portion of the body being scanned, to enhance the image produced by the MRI scanning, of a charged, stable organic nitroxide which is neurologically acceptable and non-toxic in the amount injected of a compound of Formula I.

Since the molar concentration of stable nitroxides generally required to achieve sufficient relaxation time of a body fluid to enhance the MRI of, e.g., blood, urine or an organ receiving blood directly from the cardiovascular system, e.g., brain, heart, kidney, liver, etc., can be calculated theoretically, the amount of a nitroxide of this invention which must be administered intravenously to achieve, after dilution by the blood of the mammal, image enhancement of the organ or fluid, can readily be determined by precalculation and routine experimentation.

Alternatively, the nitroxide can be stored in dry form in a conventional sealed vial, either alone or in admixture with a conventional solution-promoting watersoluble compound and formed into the desired injectable solution just prior to injection.

Conventional MRI scanning procedures can be employed in the method of this invention, e.g., those described by DiChino, G., et al., Radiology 1985, 157:373-7; and Portugal, F. H., High Technology Aug. 1984, 66–73.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, are hereby incorporated by reference.

EXAMPLES

Example 1

3-Trimethylaminomethyl-2,2,5,5-tetramethylpyrrolidine-1-oxyl iodide

4-Oxo-2,2,6,6-tetramethylpiperidine (I). In a 500 mL erlenmeyer flask, 25 gm (0.182 moles) of phorone (Aldrich Chemical Company) and 250 mL of ammonium hydroxide are stirred in a water bath at 50° C. for 14 hours. Upon cooling in an ice bath, the reaction is acidified with conc. HCl and extracted (four times) with ether. The remaining water solution is first made basic with ammonium hydroxide, then saturated with NaCl and finally, extracted with ether. The ether solution is dried over anhydrous $MgSO_4$ and evaporated to dryness, giving a pale yellow solid (I), (17 gm, 60%). A small portion of this material is recrystallized from cyclohexane, mp 34°–36° C. (lit. ref. 1) mp 35.5°–36° C.). The NMR and i.r. (1750 cm$^{-1}$) confirm the presence of 4-oxo-2,2,6,6-tetramethylpiperidine.

(1) E. G. Rozantsev, *Free Nitroxyl Radicals*, p. 203, Plenum Press, 1970.

3,5-Dibromo-4-oxo-2,2,6,6-tetramethylpiperidine Hydrobromide (II). 4-Oxo-2,2,6,6-tetramethylpiperidine (I, 17 gm, 0.110 moles) is dissolved in glacial acetic acid (70 mL). Once completed, the solution is cooled in an ice bath to which bromine (36 gm) in glacial acetic acid (50 mL) was rapidly added. After addition of bromine, the solution solidifies. The reaction is allowed to stand at room temperature, at which point, the solid dissolves and with time a new solid appears. One should allow this process to take place for at least one day, but certainly no longer than two days. The solid (II) is then filtered, washed with ether and air-dried to give 30 gm (67%) of the desired hydrobromide, which was used without recrystallization as discussed in reference 1.

3-Carbamoyl-2,2,5,5-tetramethylpyrroline (III). 3,5-Dibromo-4-oxo-2,2,6,6-tetramethylpiperidine (II, 30 gm) was added slowly, with stirring, to ammonium hydroxide (500 mL). When the solid is dissolved, potassium hydroxide is added, which results in the precipitation of (III). After filtering the solid, additional potassium hydroxide is added to the remaining solution until the precipitation of more material no longer is observed. The precipitates are combined, dried and recrystallized from benzene, giving a white solid (III, 10 gm, 68%) mp 176°–178° C. (lit ref. [1, except pg. 204] mp 180°–181° C). Both I.R. and NMR confirm the structure of (III).

3-Carbamoyl-2,2,5,5-tetramethylpyrrolidine (IV). 3-Carbamoyl-2,2,5,5-tetramethylpyrroline (III, 10 gm) was dissolved in methanol (100 mL) and reduced with hydrogen using Raney Nickel as a catalyst. Care should be taken when working with Raney Nickel, since sparking can lead to a fire. The reaction was followed by monitoring the uptake of hydrogen and the disappearance of the double bond (by NMR). When completed, the reaction was carefully filtered, and evaporated to dryness giving (IV) as a solid (~10 gm), a portion of which was recrysrystallized from benzene, mp 116°–118° C. [ref. 1, pg. 204].

3-Carbamoyl-2,2,5,5-tetramethylpyrrolidine-1-oxyl (V). 3-Carbamoyl-22,5,5-tetramethylpyrrolidine (IV, 10 gm, 0.053 moles) was dissolved in methanol/water (1:10), to which EDTA (0.56 gm) and sodium tungstate dihydrate (0.56 gm, Aldrich Chemical Company) was added. Then, hydrogen peroxide (30%, 14 mL) was added. The solution immediately became yellow. The reaction was allowed to stand at room temperature for 1 week. The solution was extracted with chloroform, washed with dilute HCl (5%) and dried over anhydrous $MgSO_4$. The chloroform solution was filtered and evaporated to dryness, giving a solid (V, 7.8 gm, 80%), mp 172°–174° C. from sublimation.

3-Carboxy-2,5,5,5-tetramethylpyrrolidine-1-oxyl (VI). Nitroxide V (7 gm, 0.0384 moles) was hydrolyzed using 15% KOH in water (100 mL) under reflux until the release of ammonia ceased (using pH paper, the pH is no longer basic). At this point, the reaction is cooled, and extracted with chloroform. The remaining water solution is cooled with ice water, made acidic with HCl (~pH 2-3), extracted with chloroform and dried over anhydrous $MgSO_4$. Upon evaporation to dryness, a yellow solid is obtained (VI, 6 gm, 85%), which is recrystallized from hexane/chloroform, mp 192°–193° C.

3-Hydroxymethyl-2,2,5,5-tetramethylpyrrolidine-1-oxyl (VII). Ethyl chloroformate (6.3 gm, 5.5 ML, 58.1 mmoles, Aldrich Chemical Company) was added slowly to a solution of 3-carboxy-2,2,5,5-tetramethylpyrrolidine-1-oxyl (VI, 10 gm, 54 mmoles) in tetrahydrofuran (freshly distilled over lithium aluminum hydride, 100 ML) and triethylamine (5.85 gm, 8.1 mL, 58.1 mmoles). After addition of ethyl chloroformate, the reaction was stirred at room temperature for 1 hour. At this point, the reaction is filtered, the filtrate washed with additional tetrahydrofuran and dried over anhydrous $Na_2SO_4$. The solution containing the mixed anhydride is added dropwise to a suspension of lithium aluminum hydride (3.8 gm, 100.5 mmoles, Aldrich Chemical Company) in tetrahydrofuran (50 mL) at 0° C. under argon. After addition of the mixed anhydride is completed, stir for an additional hour at this temperature, quench with water (5 mL) and stir overnight at room temperature in the presence of air (which oxidizes any hydroxylamine to the nitroxide). Upon filtering the mixture and extensive washing with ether, the combined solution is dried over anhydrous $Na_2SO_4$ and evaporated to dryness, giving a yellow solid (VII, 6.5 gm, 70%). A portion of which was recrystallized from ether/hexane, mp 110°–112° C. (lit. ref. 2).

(2) K. Hideg et al., *Synthesis*, pp. 911–914, 1980.

3-Carboxyaldehyde-2,2,5,5-tetramethylpyrrolidine-1-oxyl (VIII). The oxidation of alcohol (VII) was undertaken using the method of Mancuso and Swern (3). First, DMSO/oxalyl chloride complex is formed by the addition of DMSO (5 gm, 63.8 mmoles) in methylene chloride (10 mL) dropwise to a solution of oxalyl chloride (4.05 gm, 2.8 mL, 31.9 mmoles, Aldrich Chemical Company) in methylene chloride (20 mL) under argon at −60° C. It is important that the rate of addition does not raise the temperature of the reaction above −55° C. After completion, the reaction is stirred for an additional 5 minutes at −60° C. Then, the alcohol (5 gm, 29 mmoles) in methylene chloride (20 mL) is added slowly so that the temperature of the reaction does not rise above −50° C. After 20 minutes, triethylamine (14.65 gm, 20 mL, 145 mmoles) in methylene chloride (20 mL) was added. Again, the temperature should not rise above −50° C. Once completed, stir for 10 minutes, then warm to room temperature, at which point water was added. The methylene chloride solution was dried over anhydrous Na₂SO₄, filtered and the solution evaporated to dryness. The remaining red oil was chromatographed by flash chromatography using silica gel, hexane/ether, 7:3 (removed a small amount of red material, non-aldehyde), followed by ether, which removed the desired aldehyde (VIII), a red oil (3.9 gm, 80%). Confirmed by i.r. and lit. references 2 and 4. Because the aldehyde is relatively unstable, it should be stored at −20° C until use.

(3) A. J. Mancuso and D. Swern, *Synthesis,* pp. 165–185, 1981.

(4) G. E. Rend et al., *J. Amer. Chem. Soc.,* 109:6163–6168, 1987.

3-(Trimethylamino)methyl-2,2,5,5-tetramethylpyrrolidine-1-oxyl Iodide (IX). Aldehyde (VIII), 2 gm, 11.8 mmoles) dissolved in methanol (10 mL) was added to a solution containing dimethylamine hydrochloride (anhydrous, 5.76 gm, 70.6 mmoles, Aldrich Chemical Company) in methanol (50 mL). The pH is raised to 7–8 with triethylamine. Then molecular sieves (3Å) are added followed by addition of sodium cyanoborohydride (0.44 gm, 7.06 mmoles). The reaction is stirred at room temperature overnight. Upon filtration, the methanol solution is evaporated to dryness, water added (100 mL) and cooled to near 0° C. Then, dilute HCl was added to drop the pH is 2–3. This solution is extracted with chloroform. The water solution is made basic with NaOH (10%) and again extracted with chloroform. The chloroform extract from the acidic solution contains unreacted aldehyde and alcohol (VII). The chloroform extract from the basic solution is dried over anhydrous MgSO₄ and evaporated to dryness, giving a yellow oil (3-dimethylaminomethyl-2,2,5,5-tetramethylpyrroline-1-oxyl, 1.6 gm, 70%). I.R. confirmed the absence of an aldehyde. Addition of methyl iodide (excess) to an ether solution of the above gave the methyl iodide salt (IX), which was recrystallized from absolute ethanol, mp 239°–240° C. with decomposition. Anal. Calc'd: C=42.24, H=7.68, N=8.21, I=37.19. Found: C=42.20, H=7.93, N=8.10, I=36.98.

Example 2

2,2,5,5-Tetramethyl-3-(1'-carboxy-propyl-2°)-pyrrolidyloxy Sodium Salt (X)

Add 1 mol. equiv. of n-butyllithium in hexane slowly with stirring at 0° C. to diisopropylamide under N₂. Cool to −78° C. and then add thereto 1 mol. eg. of t-butyltrimethylsilyl acetate. Stir for 20 min. at that temperature and then add thereto I mol. equiv. of nitroxide (VIII) to produce 2,2,5,5-tetramethyl-3-[1'-methyl-2'-(carbo-t-butoxy)-vinyl-pyrrolidinyl-1-oxy.

Allow the temperature to rise to −2° C., stir for one hour, allow to warm to 0° and then add thereto a concentrated solution of NH₄Cl. Isolate the product and simultaneously hydrogenate the double bond and reduce to nitroxide group to an amine with H₂ and Pd/C, followed by reoxidation of the latter with H₂O₂, using sodium tungstate as oxidation catalyst. Hydrolyze the ester group with a 10% molar excess of NaOH to give the sodium salt of the desired product. Neutralize the solution with HCl and extract the free acid form of the desired product (X) with ether.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A charged, stable organic nitroxide of the formula:

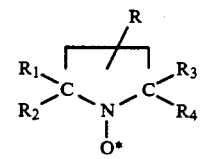

wherein $R_1$, $R_2 R_3$ and $R_4$ each are alkyl of 1–4 carbon atoms; and R is —alk—COO⁻M⁺ or —B—N⁺(Alk)₃Hal⁻ in which alk is alkylene of 1–8 carbon atoms, B is a bond or alkylene of 1–8 carbon atoms, M⁺ is an ammonium or metal ion, Alk is alkyl of 1–8 carbon atoms or a corresponding alkyl group substituted by a free or esterified hydroxy group, and Hal⁻ is Cl⁻, Br⁻ or I⁻.

2. A nitroxide according to claim 1, wherein $R_1$, $R_2$, and $R_3$ each are CH₃.

3. A nitroxide according to claim 1, wherein R is —B—N⁺(Alk)₃Hal⁻ as defined therein.

4. A nitroxide according to claim 3, wherein $R_1$, $R_2$, $R_3$ and $R_4$ each are CH₃.

5. A nitroxide according to claim 3, wherein $R_1$, $R_2$, $R_3$ and $R_4$ each are CH₃, wherein alk is alkylene of 1–4 carbon atoms and wherein Alk is alkyl of 1 to 4 carbon atoms.

6. A nitroxide according to claim 1, wherein the nitroxide is 3-(N,N,N-dimethylmethylamino)-2,2,5,5-tetramethylpyrrolidin-1-oxyl iodide.

7. A nitroxide according to claim 1, wherein the nitroxide is 3-(trimethylamino)-2,2,5,5-tetramethylpyrrolidin-1-oxyl iodide.

8. A nitroxide according to claim 1, wherein R is —alk—COO⁻M⁺ as defined therein.

9. A nitroxide according to claim 8, wherein $R_1$, $R_2$, $R_3$ and $R_4$ each are CH₃.

10. A nitroxide according to claim 8, wherein $R_1$, $R_2$, $R_3$ and $R_4$ each are CH₃ and B is alkylene of 1 to 4 carbon atoms.

11. A nitroxide according to claim 8, wherein $R_1$, $R_2$, $R_3$ and $R_4$ each are CH₃, wherein alk is alkylene of 2 to 4 carbon atoms, and wherein M⁺ is Na⁺ or K⁺.

12. A nitroxide according to claim 1, wherein the nitroxide is the sodium salt of 2,2,5,5-tetramethyl-3-(1'-carboxy-propyl-2')pyrrolidyl-1-oxy.

* * * * *